(12) United States Patent
Livshits et al.

(10) Patent No.: US 7,527,950 B2
(45) Date of Patent: May 5, 2009

(54) **METHOD FOR PRODUCING AN L-AMINO ACID BY ENHANCING EXPRESSION OF THE YFIK GENE IN AN *ESCHERICHIA* BACTERIUM**

(75) Inventors: Vitaliy Arkadievich Livshits, Moscow (RU); Natalia Pavlovna Zakataeva, Moscow (RU); Kazuo Nakanishi, Yokohama (JP); Vladimir Veniaminovich Aleshin, Moscow (RU); Petr Vladimirovich Troshin, Moscow (RU); Irina Lyvovna Tokhmakova, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/854,850

(22) Filed: Sep. 13, 2007

(65) Prior Publication Data

US 2008/0050784 A1 Feb. 28, 2008

Related U.S. Application Data

(60) Division of application No. 11/276,522, filed on Mar. 3, 2006, now Pat. No. 7,399,617, which is a division of application No. 11/116,286, filed on Apr. 28, 2005, now abandoned, which is a continuation of application No. 09/459,573, filed on Dec. 13, 1999, now Pat. No. 6,979,560.

(30) Foreign Application Priority Data

Dec. 30, 1998 (RU) ................................. 98124016
Mar. 9, 1999 (RU) ................................. 99104431

(51) Int. Cl.
| | |
|---|---|
| *C12P 13/04* | (2006.01) |
| *C12P 13/24* | (2006.01) |
| *C12P 13/14* | (2006.01) |
| *C12P 13/08* | (2006.01) |
| *C12N 1/21* | (2006.01) |
| *C12N 15/00* | (2006.01) |
| *C12P 21/06* | (2006.01) |

(52) U.S. Cl. ...................... 435/106; 435/115; 435/110; 435/107; 435/69.1; 435/320.1; 435/252.33; 435/252.3; 435/440; 530/350; 536/23.1

(58) Field of Classification Search ................ 435/69.1, 435/320.1, 440, 110, 115, 107, 252.33, 252.3; 530/350; 536/23.1
See application file for complete search history.

(56) References Cited

U.S. PATENT DOCUMENTS

| | | | |
|---|---|---|---|
| 5,175,107 A | 12/1992 | Debabov et al. |
| 5,538,873 A | 7/1996 | Debabov et al. |
| 5,631,157 A | 5/1997 | Debabov et al. |
| 5,658,766 A | 8/1997 | Livshits et al. |
| 5,705,371 A | 1/1998 | Debabov et al. |
| 5,976,843 A | 11/1999 | Debabov et al. |
| 6,040,160 A | 3/2000 | Kojima et al. |
| 6,132,999 A | 10/2000 | Debabov et al. |
| 6,165,756 A | 12/2000 | Debabov et al. |
| 6,303,348 B1 | 10/2001 | Livshits et al. |
| 6,653,111 B2 | 11/2003 | Debabov et al. |
| 6,737,255 B2 | 5/2004 | Livshits et al. |
| 6,858,406 B1 | 2/2005 | Vrlijc et al. |
| 6,887,691 B2 | 5/2005 | Livshits et al. |
| 6,960,455 B2 | 11/2005 | Livshits et al. |
| 6,979,560 B1 | 12/2005 | Livshits et al. |
| 7,138,266 B2 | 11/2006 | Debabov et al. |
| 7,179,623 B2 | 2/2007 | Livshits et al. |
| 7,259,003 B2 | 8/2007 | Livshits et al. |
| 2001/0049126 A1 | 12/2001 | Livshits et al. |
| 2002/0058314 A1 | 5/2002 | Livshits et al. |
| 2002/0160461 A1 | 10/2002 | Nakai et al. |
| 2005/0239177 A1 | 10/2005 | Livshits et al. |
| 2006/0014258 A1 | 1/2006 | Livshits et al. |
| 2006/0030009 A1 | 2/2006 | Livshits et al. |
| 2006/0040364 A1 | 2/2006 | Livshits et al. |
| 2007/0166807 A1 | 7/2007 | Tokhmakova et al. |

FOREIGN PATENT DOCUMENTS

| | | |
|---|---|---|
| EP | 0 994 190 | 4/2000 |
| WO | WO97/23597 | 7/1997 |

OTHER PUBLICATIONS

Kozak, M., "Initiation of translation in prokaryotes and eukaryotes," Gene 1999;234:187-208.

Zhou, D., et al., "Global analysis of gene transcription regulation in prokaryotes," Cell. Mol. Life Sci. 2006;63:2260-2290.

Alefounder, P. R., et al., Accession: P11667 [GI: 140686], Definition: Hypothetical 21.7 KD Protein in FBA/FDA 5'Region (ORF 5). Publication Date: Jul. 21, 1998.

Blattner, F. R, et al., Accession: P76249 [GI: 3025145], Definition: Hypothetical 23.2 KD Protein in GAPA-RND Intergenic Region. Publication Date: Jul. 21, 1998.

(Continued)

*Primary Examiner*—Delia M Ramirez
(74) *Attorney, Agent, or Firm*—Shelly Guest Cermak; Cermak Kenealy Vaidya & Nakajima LLP

(57) ABSTRACT

A bacterium belonging to the genus *Escherichia* which has an ability to produce an L-amino acid, wherein the ability to produce the L-amino acid is increased by increasing expression of the yfiK gene is described. A method for producing the L-amino acid using the bacterium is also described.

8 Claims, No Drawings

OTHER PUBLICATIONS

Cossart, P., et al., "Nucleotide sequence of the thrB gene of *E. coli*, and its two adjacent regions; the thrAB and thrBC junctions," Nuc. Acids Res. 1981;9(2):339-347.

Katinka, M., et al., "Nucleotide sequence of the thrA gene of *Escherichia coli*," Proc. Natl. Acad. Sci. USA 1980;77(10):5730-5733.

Nashimoto, H., Accession: P38101 [GI: 586624], Definition: Hypothetical 21.2 KD Protein in SRMB-UNG Intergenic Region. Publication Date: Dec. 18, 1998.

Office Action [Notice of Reason for Rejection] from Japanese Patent App. No. 11-373651 (Jul. 31, 2007) and English translation thereof.

Aiba, H., et al., "Non-Ribosomal Proteins Affecting the Assembly of Ribosomes in *Escherichia coli*," Database EMBL/Swissprot (Online) ID: YFIK_ECOLI, Oct. 1, 1994.

Alefounder, P. R., et al., "Identification, Molecular Cloning and Sequence Analysis of a Gene Cluster Encoding the Class II Fructose 1,6-Bisphosphate Aldolase, 3-Phosphoglycerate Kinase and a Putative Second Gluceraldehyde 3-Phosphate Dehydrogenase of *Escherichia coli*," Database EMBL/Swissprot (Online) ID: YGGA_ECOLI, Oct. 1, 1989.

Aleshin, et al., Trends Biochem. Sci. 1999;24(4):133-135.

Blattner, F.R., et al., "The Complete Genome Sequence of *Escherichia coli* K-12," Science 1997;277:1-8, Acc. AE000344, Definition = *Escherichia coli* K-12 MG1655 section 234 of 400 of the complete genome.

Blattner, F.R., et al., "The Complete Genome Sequence of *Escherichia coli* K-12," Science 1997;277:1-7, Acc. AE000375, Definition = *Escherichia coli* K-12 MG1655 section 265 of 400 of the complete genome.

Blattner, F.R., et al., "The Complete Genome Sequence of *Escherichia coli* K-12," Science 1997;277:1-9, Acc. AE000140, Definition = *Escherichia coli* K-12 MG1655 section 30 of 400 of the complete genome.

Blattner, F.R., et al., "The Complete Genome Sequence of *Escherichia coli* K-12," Science 1997;277:1-10, Acc. AE000274, Definition = *Escherichia coli* K-12 MG1655 section 164 of 400 of the complete genome.

Blattner, F.R., et al., GenBank Accession No. P75693, Nov. 1, 1997.

Branden, C., et al., Introduction to Protein Structure, Garland Publishing, Inc., New York, pp. 247, 1991.

Current Protocols in Molecular Biology, Hybridization Analysis of DNA Blots, pp. 2.10.8-2.10.11, 1993.

Duncan, M., et al., "The Complete Genome Sequence of *Escherichia coli* K-12," Database EMBL/Swissprot (Online) ID: Yahn-Ecoli, Nov. 1, 1997.

Itoh, T., et al., "A 460-kb DNA Sequence of the *Escherichia coli* K-12 Genome Corresponding to the 40.1-50.0 Min Region on the Linkage Map," Database EMBL/Swissprot (Online) ID: YEAS_ECOLI, Jul. 15, 1998.

"LysE," Pfam 7.0, Accession No. PF01810.

Seffernick, J. L., et al., "Melamine Deaminase and Atrazine Chlorohydrolase: 98 Percent Identical but Functionally Different," J. Bacteriol. 2001;183(8):2405-2410.

Vrljic, M., et al., Mol. Microbiol. 1996;22(5):815-826.

Witkowski, A., et al., "Conversion of a β-Ketoacyl Synthase to a Malonyl Decarboxylase by Replacement of the Active-Site Cysteine with Glutamine," Biochem. 1999;38:11643-11650.

Zakataeva, N. P., et al., "Characterization of a Pleiotropic Mutation That Confers Upon *Escherichia coli* Cells Resistance to High Concentrations of Homoserine and Threonine," FASEB Journal 1997;11(9):A935.

Meinnel, T., et al., "Discrimination by *Escherichia coli* Initiation Factor IF3 Against Initiation on Non-canonical Codons Relies on Complementary Rules," J. Mol. Biol. 1999;290:825-837.

Nandineni, M. R., et al., "Evidence for an Arginine Exporter Encoded by *yggA* (*argO*) That Is Regulated by the LysR-Type Transcriptional Regulator ArgP in *Escherichia coli*," J. Bacteriol. 2004;186(11):3539-3546.

METHOD FOR PRODUCING AN L-AMINO ACID BY ENHANCING EXPRESSION OF THE YFIK GENE IN AN *ESCHERICHIA* BACTERIUM

This application claims the benefit as a divisional application under 35 U.S.C. §120 to application Ser. No. 11/276,522, filed Mar. 3, 2006, which is now U.S. Pat. No. 7,399,617, issued Jul. 15, 2008, which is a divisional of abandoned application Ser. No. 11/116,286, filed Apr. 28, 2005, which is a continuation of application Ser. No. 09/459,573, filed Dec. 13, 1999,which is now U.S. Pat. No. 6,979,560, issued Dec. 27, 2005, which claimed priority under 35 U.S.C. §119 to Russian Patent Application No. 98124016, filed Dec. 30, 1998, and Russian Patent Application No. 99104431, filed on Mar. 9, 1999.

BACKGROUND OF THE INVENTION

1. Field of the Invention

The present invention relates to a method for producing an amino acid. In particular, the present invention relates to an L-amino acid-producing bacterium belonging to the genus *Escherichia* and a method for producing L-amino acids using the bacterium, more specifically, L-glutamic acid, L-lysine, L-threonine, L-alanine, L-histidine, L-proline, L-arginine, L-valine, and L-isoleucine.

2. Brief Description of the Related Art

To improve production of L-amino acids by fermentation, strains isolated from nature or artificial mutants thereof have been used. For example, many artificial mutants which produce L-lysine are known, and most of them are resistant to S-2-aminoethylcysteine (AEC) and belong to the genus *Brevibacterium, Corynebacterium, Bacillus*, or *Escherichia*. Also, various techniques have been proposed to increase amino acid production, such as using a strain which has been transformed with recombinant DNA (U.S. Pat. No. 4,278, 765).

The reported techniques are largely based on enhancing an activity of an enzyme involved in an amino acid biosynthetic pathway, conversion of the enzyme to one that is desensitized in inhibition, and the like (As to bacterium belonging the genus *Escherichia*, see Japanese Patent Application Laid-Open No. 56-18596 (1981) and International Publication No. WO 95/16042).

Alternatively, a bacterium belonging to the genus *Corynebacterium* in which the L-lysine excretion gene lysE is enhanced is known, and is an example of improving amino acid productivity by enhancing an amino acid excretion protein. However, as to bacteria belonging to the genus *Escherichia*, it is unknown whether an L-amino acid excretion protein exists or not. Therefore, it is unknown whether or not enhancing an L-amino acid excretion protein would be effective for L-amino acid production when using a bacterium belonging to the genus *Escherichia*.

Although the entire nucleotide sequence of *E. coli* strain K-12 has been determined (Science, 277, 1453-1474 (1997)), there are a large number of proteins for which their functions remain unknown.

SUMMARY OF THE INVENTION

An object of the present invention is to obtain a protein which participates in excretion of an L-amino acid, and thereby provide a strain which has improved L-amino acid productivity. Another object of the present invention is to provide an improved method for producing an L-amino acid by fermentation.

The inventors have conducted screening for a protein which participates in excretion of an L-amino acid. As a result, the present inventors have found that the yield of an L-amino acid based on consumed sugar increases when a particular gene is enhanced. On the basis of this finding, the present invention has been completed.

Thus, the present invention provides a bacterium belonging to the genus *Escherichia* (hereinafter "the bacterium of the present invention") which has an ability to produce an L-amino acid, wherein the ability to produce the L-amino acid increases by increasing the expression of at least one protein selected from the group consisting of:

(A) a protein comprising an amino acid sequence shown in SEQ ID NO: 10;

(B) a protein comprising an amino acid sequence of SEQ ID NO: 10, and which includes deletion, substitution, insertion, addition, or inversion of one or several amino acids in said amino acid sequence, and which has an activity of increasing the ability of the bacterium having the protein to produce the L-amino acid;

(C) a protein comprising an amino acid sequence shown in SEQ ID NO: 12;

(D) a protein comprising an amino acid sequence of SEQ ID NO: 12, and which includes deletion, substitution, insertion, addition, or inversion of one or several amino acids in said amino acid sequence, and which has an activity of increasing the ability of the bacterium having the protein to produce the L-amino acid;

(E) a protein comprising an amino acid sequence shown in SEQ ID NO: 14;

(F) a protein comprising an amino acid sequence of SEQ ID NO: 14, and which includes deletion, substitution, insertion, addition, or inversion of one or several amino acids in said amino acid sequence, and which has an activity of increasing the ability of the bacterium having the protein to produce the L-amino acid;

(G) a protein comprising an amino acid sequence shown in SEQ ID NO: 16; or (H) a protein comprising an amino acid sequence of SEQ ID NO: 16, and which includes deletion, substitution, insertion, addition, or inversion of one or several amino acids in said amino acid sequence, and which has an activity of increasing the ability of the bacterium having the protein to produce the L-amino acid.

The bacterium of the present invention is preferably an L-lysine-producing bacterium in which expression of at least one protein selected from the group consisting of the proteins (A) to (D), (G) and (H) is increased; an L-glutamic acid-producing bacterium in which expression of at least one protein selected from the group consisting of the proteins (A) to (H) is increased; an L-alanine-producing bacterium in which expression of at least one protein selected from the group consisting of the proteins (C) and (D) is increased; an L-valine-producing bacterium in which expression of at least one protein selected from the group consisting of the proteins (C) and (D) is increased; an L-histidine-producing bacterium in which expression of at least one protein selected from the group consisting of said proteins (C) to (F) is increased; an L-proline-producing bacterium in which expression of at least one protein selected from the group consisting of said proteins (A) to (F) is increased; an L-threonine-producing bacterium in which expression of at least one protein selected from the group consisting of said proteins (E) and (F) is increased; an L-arginine-producing bacterium in which expression of at least one protein selected from the group consisting of said proteins (G) and (H) is increased; or an L-isoleucine-producing bacterium in which expression of at least one protein selected from the group consisting of said proteins (C) and (D) is increased.

Preferably, in the bacterium of the present invention, the copy number of a DNA coding for said protein is increased. The DNA is preferably carried on a multicopy vector or on a transposon in the cell.

The present invention also provides a method for producing an L-amino acid comprising cultivating the bacterium of the present invention in a culture medium, and recovering the L-amino acid from the medium (hereinafter also referred to as "the method of the present invention").

The method of the present invention is preferably an L-lysine production method using an L-lysine-producing bacterium in which expression of at least one protein selected from the group consisting of the proteins (A) to (D), (G) and (H) is increased; an L-glutamic acid production method using an L-glutamic acid-producing bacterium in which expression of at least one protein selected from the group consisting of the proteins (A) to (H) is increased; an L-alanine production method using an L-alanine-producing bacterium in which expression of at least one protein selected from the group consisting of the proteins (C) and (D) is increased; an L-valine production method using an L-valine-producing bacterium in which expression of at least one protein selected from the group consisting of the proteins (C) and (D) is increased; an L-histidine production method using an L-histidine-producing bacterium in which expression of at least one protein selected from the group consisting of said proteins (C) to (F) is increased; an L-proline production method using an L-proline-producing bacterium in which expression of at least one protein selected from the group consisting of said proteins (A) to (F) is increased; an L-threonine production method using an L-threonine-producing bacterium in which expression of at least one protein selected from the group consisting of said proteins (E) and (F) is increased; an L-arginine production method using an L-arginine-producing bacterium in which expression of at least one protein selected from the group consisting of said proteins (G) and (H) is increased; or an L-isoleucine production method using an L-isoleucine-producing bacterium in which expression of at least one protein selected from the group consisting of said proteins (C) and (D) is increased.

Preferably, in the method of the present invention, a copy number of a DNA coding for said protein in the bacterium is increased. The DNA is preferably carried on a multicopy vector or on a transposon in the cell.

According to the present invention, an ability of a bacterium belonging to the genus *Escherichia* to produce an L-amino acid is increased. Also, a method for producing an L-amino acid is improved by increasing the production rate of the L-amino acid.

DETAILED DESCRIPTION OF THE PREFERRED EMBODIMENTS

The present invention will be explained in detail below. Hereinafter, an amino acid is of the L-configuration unless otherwise noted.

<1> Bacterium of the Present Invention

The bacterium of the present invention is a bacterium belonging to the genus *Escherichia* which has an ability to produce an amino acid. The ability to produce the amino acid is increased by increasing expression of a protein which has an activity of increasing the ability to produce the amino acid of the bacterium, or an activity of increasing resistance to an amino acid or amino acid analogue. Hereinafter, the protein is referred to as "amino acid excretion protein". However, the term does not mean that function of the protein is limited to amino acid excretion.

Examples of the amino acid excretion protein include a protein having an amino acid sequence shown in SEQ ID NO: 10, a protein having an amino acid sequence shown in SEQ ID NO: 12, a protein having an amino acid sequence shown in SEQ ID NO: 14, and a protein having an amino acid sequence shown in SEQ ID NO: 16.

The amino acid excretion protein may be selective for a particular amino acid. An amino acid excretion protein appropriate for each amino acid can be determined by expressing the protein in an *Escherichia* bacterium which has the ability to produce the amino acid, and measuring the increased yield of the amino acid, or measuring the increased minimum inhibition concentration (MIC) of the amino acid or an amino acid analogue.

For example, for lysine, a protein having an amino acid sequence shown in SEQ ID NO: 10, 12, or 16 is effective; for glutamic acid, a protein having an amino acid sequence shown in SEQ ID NO: 10, 12, 14, or 16 is effective; for alanine, a protein having an amino acid sequence shown in SEQ ID NO: 12 is effective; for valine, a protein having an amino acid sequence shown in SEQ ID NO: 12 is effective; for histidine, a protein having an amino acid sequence shown in SEQ ID NO: 12 or 14; for proline, a protein having an amino acid sequence shown in SEQ ID NO: 10, 12, or 14 is effective; for threonine, a protein having an amino acid sequence shown in SEQ ID NO: 14 is effective; for arginine, a protein having an amino acid sequence shown in SEQ ID NO: 16 is effective; for isoleucine, a protein having an amino acid sequence shown in SEQ ID NO: 12 is effective.

The phrase "expression is increased" used herein usually means that the expression amount is larger than that in a wild-type strain of *E. coli*, such as the strains MG1655 or W3110. The phrase also means that when a strain is modified by genetic engineering techniques or the like, the expression amount is larger than that prior to the modification. Expression of the amino acid excretion protein may be determined directly by measuring the protein amount, or indirectly by measuring the MIC of the amino acid or an amino acid analogue, or measuring the amino acid productivity of the *Escherichia* bacterium.

The method for increasing expression of the amino acid excretion protein is exemplified by increasing a copy number of a DNA encoding the amino acid excretion protein in the bacterium.

To increase the copy number in the cell, a DNA fragment coding for the amino acid excretion protein may be ligated to a vector which functions in the chosen *Escherichia* bacterium to produce a recombinant DNA, which is introduced into a host to transform it. The copy number of the gene coding for the amino acid excretion protein (amino acid excretion protein gene) in the cell of the transformant strain increases, thereby increasing the expression amount of the amino acid excretion protein. The vector is preferably a multicopy vector.

The increase of the copy number in the cell can be achieved by allowing plural copies of the amino acid excretion protein gene to exist on the chromosomal DNA of the host. The introduction of plural copies of the amino acid excretion protein gene to the chromosomal DNA of the *Escherichia* bacterium, may be acheived via homologous recombination using a target sequence of which plural copies exist on the chromosomal DNA. As said target sequence, a repetitive DNA and an inverted repeat present in a terminal portion of a transposable element may be used. Alternatively, as disclosed in Japanese Patent Application Laid-Open No. 2-109985 (1990), plural copies can be introduced to the chromosomal DNA by carrying the amino acid excretion protein gene on a transposon and allowing the transposon to be transposed, which is preferred. According to any of the above-mentioned methods, the copy number of the amino acid excretion protein gene in the transformant strain increases, thereby increasing expression of the amino acid excretion protein.

The multicopy vector is exemplified by plasmid vectors such as pBR322, pMW118, pUC19, or the like, and phage vectors such as λ1059, λBF101, M13 mp9, or the like. The transposon is exemplified by Mu, Tn10, Tn5, or the like.

To introduce a DNA into an *Escherichia* bacterium, for example, the method of D. M. Morrison (Methods in Enzymology 68, 326 (1979)), or a method in which recipient bacterial cells are treated with calcium chloride to increase permeability of DNA (Mandel, M. and Higa, A., J. Mol. Biol., 53, 159 (1970)), and the like can be used.

Besides the above-mentioned gene amplification, increasing expression of the amino acid excretion protein can be also achieved by replacing an expression regulatory sequence, such as a promoter of the amino acid excretion protein gene, with stronger one (see Japanese Patent Application Laid-Open No. 1-215280 (1989)). For example, lac promoter, trp promoter, tac promoter, $P_R$ promoter and $P_L$ promoter of lambda phage, and the like are known as a strong promoters. Replacing the promoter enhances expression of the amino acid excretion protein, thereby increasing expression of the amino acid excretion protein. Enhancing the expression regulatory sequence may be combined with increasing the copy number of the amino acid excretion protein.

In the bacterium of the present invention, expression of plural amino acid excretion proteins may be increased.

The amino acid excretion protein is encoded by genes which are known as the yahN gene, yeaS gene, yfiK gene, and yggA gene. The functions of these genes are unknown. Therefore, the DNA encoding the amino acid excretion protein can be obtained by synthesizing primers based on the known sequences (for example, the entire nucleotide sequence of the chromosome of *Escherichia coli* strain K-12 has been determined (Science, 277, 1453-1474 (1997))), and amplifying by PCR using chromosomal DNA of an *Escherichia* bacterium as a template. Also, the object DNA fragment can be selected by hybridization from an *Escherichia* bacterium chromosomal DNA library by preparing a probe based on the known sequences. Alternatively, the DNA encoding the amino acid excretion protein may be synthesized based on the known sequences. The nucleotide sequence of the DNA encoding the amino acid excretion protein is exemplified by those shown in SEQ ID NOs: 9, 11, 13, or 15.

Methods for preparation of a chromosomal DNA, preparation of a chromosomal DNA library, hybridization, PCR, preparation of plasmid DNA, digestion and ligation of DNA, transformation, selection of an oligonucleotide as a primer, and the like may be performed by ordinary methods well known to those skilled in the art. These methods are described in Sambrook, J., Fritsch, E. F., and Maniatis, T., "Molecular Cloning A Laboratory Manual, Second Edition", Cold Spring Harbor Laboratory Press (1989) and the like.

The amino acid excretion protein may include substitution, deletion, insertion, addition, or inversion of one or several amino acids at one or a plurality of positions, provided that the activity of increasing the ability of the *Escherichia* bacterium having the protein to produce the amino acid is not deteriorated. The number intended by the term "several" may vary depending on the position in the steric structure of the protein and the kind of amino acid residue. This is because some amino acids such as isoleucine and valine are highly similar, and interchanging such amino acids does not largely affect the steric structure of the protein.

The DNA which codes for substantially the same protein as the amino acid excretion protein as described above, may be obtained, for example, by modifying the nucleotide sequence, for example, by means of site-directed mutagenesis so that one or more amino acid residues at a specified site are substituted, deleted, inserted, added, or inverted. The DNA modified as described above may be obtained by a conventionally known mutation treatment. Such a mutation treatment includes treating a DNA coding for the amino acid excretion protein in vitro, for example, with hydroxylamine, and treating a microorganism, for example, a bacterium belonging to the genus *Escherichia*, harboring a DNA coding for the amino acid excretion protein with ultraviolet irradiation or a mutating agent, such as N-methyl-N'-nitro-N-nitrosoguanidine (NG) and nitrous acid, which are usually used for mutation treatments.

The substitution, deletion, insertion, addition, or inversion of one or more amino acid residues includes a naturally-occurring mutation or variation which results from differences between individual microorganisms having the amino acid excretion protein, and differences between species, strains, or the like.

The DNA which codes for substantially the same protein as the amino acid excretion protein can be obtained by allowing a DNA having the mutation as described above to be expressed in an appropriate *Escherichia* bacterium, and investigating the increase of amino acid productivity of the cell.

Also, the DNA which codes for substantially the same protein as the amino acid excretion protein can be obtained by isolating a DNA which hybridizes with, for example, a nucleotide sequence shown in SEQ ID NO: 9, 11, 13, or 15 under stringent conditions, and which DNA codes for a protein having the activity of increasing the ability of the bacterium belonging to the genus *Escherichia* to produce the amino acid, from DNAs encoding the amino acid excretion proteins having mutations or cells containing the DNAs. The term "stringent conditions" referred to herein means conditions under which a specific hybrid is formed, and a non-specific hybrid is not formed. It is difficult to clearly express this condition by using any numerical value. However, for example, the stringent conditions include conditions under which DNAs having high homology, for example, DNAs having homology of not less than 70% with each other are hybridized, and DNAs having homology with each other lower than the above are not hybridized, or conditions comprising washing in a salt concentration corresponding to 60° C., 1×SSC, 0.1% SDS, preferably 0.1×SSC, 0.1% SDS, which is ordinary washing conditions for Southern hybridization.

Although there may be a gene in which a stop codon is located in the middle, or a gene encoding a protein which has lost activity due to mutation of the active center among the genes which hybridize under such the condition, such genes can be easily eliminated by ligating the genes to a commercially available activity-expression vector and determining the activity of the bacterium belonging to the genus *Escherichia* to increase the ability to produce the amino acid as described above.

The term "DNA coding for a protein" used herein means a DNA of which one of strands codes for the protein when the DNA is double-stranded.

By increasing expression of an amino acid excretion protein in an amino acid-producing Escherichia bacterium as described above, the amount of the amino acid produced can be increased. As the Escherichia bacterium which has increased expression of the amino acid excretion protein, strains which have abilities to produce desired amino acids (amino acid productivities) are used. Besides, an ability to produce an amino acid may be imparted to a bacterium in which expression of the amino acid excretion protein is increased. Examples of amino acid-producing bacteria belonging to the genus Escherichia include E. coli AJ13199 (FR patent No. 2747689), and those obtainable from known materials (e.g., E. coli W3110 (tyrA)/pCABD2, E. coli VL614, E. coli VL2054, E. coli VL2160, E. coli VL2151, E. coli W3350 argE::Tn10/pKA10 as described in the Examples below).

For reference, the amino acid excretion protein according to the present invention was identified for the first time as described below.

The present inventors have identified rhtB and rhtC as threonine excretion protein genes of a bacterium belonging to the genus Escherichia. The present inventors searched databases based on a hypothesis that amino acid excretion proteins may share a common structure. Namely, BLAST and PSI-BLAST search (Altschul, S. F. et al., Nucleic Acids Res., 25, 3389-3402 (1997)) for homology of a protein encoded by rhtB was performed in GenBank CDS, PDB, SWISS-PROT, Spupdate, and PIR. Tblastn search was performed in unfinished microbial genomes. BLITZ search (Sturrock, S. S., and Collins, J. F., Mpsch version 1.3. Biocomputing research unit University of Edinburgh, UK (1993)) was performed in SWALL database. SMART search (Ogiwara, I. et al., Protein Sci., 5, 1991-1999 (1996)) was performed in the databases of translations and SWISS-PROT. From the samples of more than 60 sequences found, YeaS (corresponding to f212 of ACCESSION No. AE000274 in GenBank), YahN (corresponding to f223 of ACCESSION No. AE000140 in GenBank), YfiK (corresponding to o195 of ACCESSION No. AE000344 in GenBank) and YggA (corresponding to f211 of ACCESSION No. AE000375 in GenBank) remained among those originating from E. coli as proteins which may have similar function to RhtB. Since the function of any of these genes was unknown, the genes were actually obtained, and effects thereof on MIC of amino acids and amino acid analogues and on amino acid production were examined by enhancing the activities thereof. As a result, an effect of increasing MIC of some amino acids and analogues was found with respect to YeaS, YfiK, YahN and YggA. Further examination has revealed that proteins encoded by these genes exhibit an effect of increasing accumulation of an amino acid, although they may have some amino acid selectivities.

<2> Method of the Present Invention

The method of the present invention includes the steps of cultivating the bacterium of the present invention in a culture medium to produce and accumulate the amino acid in the medium, and recovering the amino acid from the medium.

Suitable amino acids include lysine, glutamic acid, alanine, valine, histidine, proline, threonine, arginine, and isoleucine.

In the method of present invention, the cultivation of the Escherichia bacterium, and the collection and purification of an amino acid from the liquid medium may be performed in a manner similar to conventional methods for producing an amino acid by fermentation using a bacterium. A medium used in cultivation may be either a synthetic medium or a natural medium, so long as the medium includes a carbon and a nitrogen source and minerals and, if necessary, nutrients which the chosen bacterium requires for growth in appropriate amounts. The carbon source may include various carbohydrates such as glucose and sucrose, and various organic acids. Depending on the assimilatory ability of the chosen bacterium, alcohols including ethanol and glycerol may be used. As the nitrogen source, ammonia, various ammonium salts such as ammonium sulfate, other nitrogen compounds such as amines, a natural nitrogen source such as peptone, soybean hydrolyte and digested fermentative microbe are used. As minerals, monopotassium phosphate, magnesium sulfate, sodium chloride, ferrous sulfate, manganese sulfate, and calcium carbonate are used.

The cultivation is preferably under aerobic conditions such as by shaking, aeration, and/or stirring. The temperature of the culture is usually 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 3-day cultivation leads to the accumulation of the target amino acid in the medium.

Recovering the amino acid can be performed by removing solids such as cells from the medium by centrifugation or membrane filtration after cultivation, and then collecting and purifying the target amino acid by ion exchange, concentration, crystalline fraction methods, and the like.

EXAMPLES

The present invention will be more concretely explained below with reference to the following non-limiting Examples.

Example 1

Preparation of the DNA Fragments which Code for Amino Acid Excretion Proteins

The entire nucleotide sequence of the chromosome of E. coli strain K-12 has been determined (Science, 277, 1453-1474, 1997). Based on the reported nucleotide sequence, primers were synthesized and the genes yahN, yfiK, yeaS and yggA were amplified by PCR.

(1). Chromosomal DNA of the E. coli Strain MG1655 was Used as a Template.

The chromosomal DNA was prepared by an ordinary method (Sambrook, J., Fritsch E. F. and Maniatis T. (1989) Molecular cloning: a laboratory manual, 2nd ed. Cold Spring Harbor Laboratory Press, Cold Spring Harbor, N.Y.). In the PCR reaction, a standard condition described in "PCR protocols. Current methods and applications". (White, B. A., ed. Humana Press, Totowa, N.J., 1993) was used. The obtained PCR products were purified by an ordinary method and digested with restriction enzymes as described below.

The yahN gene was amplified by using primers No. 1 and No. 2.

Primer No. 1: gtgtggaaccgacgccggat (a sequence complementary to a sequence from nucleotide numbers 1885 to 1904 in the nucleotide sequence registered under ACCESSION No. AE000140 in GenBank; SEQ ID NO: 17), and Primer No. 2: tgttgtatggtacggggttcgag (a sequence from nucleotide numbers 223 to 245 in the same; SEQ ID NO: 18).

The obtained PCR product after purification was digested with restriction enzymes PstI and StuI and ligated to vector pUC21 (Vieira, Messing, Gene, 100, 189-194, 1991), and digested with the enzymes PstI and EcoRV by using a ligation kit. Then, transformation of competent cells of E. coli TG1

(Sambrook, J., Fritsch E. F. and Maniatis T. (1989) Molecular cloning: a laboratory manual, 2nd ed. Cold Spring Harbor Laboratory Press, Cold Spring Harbor, N.Y.) with the product was conducted and the cells were spread on L medium (10 g/l Bacto trypton, 5 g/l Yeast extract, 5 g/l NaCl, 15 g/l agar, pH 7.0) containing 10 μg/ml IPTG (isopropyl-β-D-thiogalacto-pyranoside) and 40 μg/ml X-gal (5-bromo-4-chloro-3-indolyl-β-D-galactoside) and 100 μg/ml ampicillin, and cultured overnight. White colonies which appeared were picked up and subjected to single colony isolation to obtain transformants. A plasmid was prepared from the transformants using an alkali extraction method and designated as pYAHN.

The yeaS gene was amplified by using primers No. 3 and No. 4.

Primer No. 3: ctttgccaatcccgtctccc (a sequence complementary to a sequence from nucleotide numbers 7683 to 7702 in a nucleotide sequence registered under ACCESSION No AE000274 in GenBank; SEQ ID NO: 19);

Primer No. 4: gccccatgcataacggaaag (a sequence from nucleotide numbers 5542 to 5561 in the same; SEQ ID NO: 20).

The obtained PCR product after purification was digested with a restriction enzyme AvaI and ligated to vector pUC19. After transformation of E. coli TG1 as above, a plasmid was obtained and designated pYEAS.

The yfiK gene was amplified by using primers No. 5 and No. 6.

Primer No. 5: gaagatcttgtaggccggataaggcg (a sequence from nucleotide numbers 4155 to 4177 in a nucleotide sequence registered under ACCESSION No AE000344 in GenBank, with a restriction enzyme BglII site added at the 5'-end thereof; SEQ ID NO: 21)

Primer No. 6: tggttttaccaattggccgc (a sequence complementary to a sequence from nucleotide numbers 6307 base to 6326 in the same; SEQ ID NO: 22).

The PCR product obtained after purification was digested with restriction enzymes BglII and MunI and ligated to vector pUC21 digested with restriction enzymes BglII and EcoRI. After transformation of E. coli TG1 as above, the plasmid designated pYFIK was obtained.

The yggA gene was amplified by using primers No. 7 and No. 8.

Primer No. 7: acttctcccgcgagccagttc (a sequence complementary to a sequence from nucleotide numbers 9606 to 9626 in a nucleotide sequence registered under ACCESSION No AE000375 in GenBank; SEQ ID NO: 23).

Primer No. 8: ggcaagcttagcgcctctgtt (a sequence from nucleotide numbers 8478 to 8498 in the same; SEQ ID NO: 24).

The PCR product obtained after purification was digested with restriction enzymes HindIII and ClaI and ligated to vector pOK12 (Vieira, Messing, Gene, 100, 189-194, 1991) digested with the same restriction enzymes. After transformation of E. coli TG1 as above, a plasmid was obtained and designated pYGGA.

(2). Chromosomal DNA of the E. coli Strain W3110 was Used as a Template.

The yahN gene was amplified by using primers No. 9 (SEQ ID NO 1) and No. (SEQ ID NO:2)

The yeaS gene was amplified by using primers No. 11 (SEQ ID NO 3) and No. 12 (SEQ ID NO 4)

The yfiK gene was amplified by using primers No. 13 (SEQ ID NO 5) and No. 14 (SEQ ID NO 6).

The yggA gene was amplified by using primers No. 15 (SEQ ID NO 7) and No. 16 (SEQ ID NO 8)

The obtained PCR product was purified, digested with restriction enzymes SacI and XbaI (EcoRI and PstI for yggA), and ligated to plasmid pMW118 (Nippon Gene). The plasmid into which a DNA fragment with an identical sequence to the reported sequence was inserted was designated as follows:

Plasmid carrying yahN: pMW118::yahN
Plasmid carrying yeaS: pMW118::yeaS Plasmid carrying yfiK: pMW118::yfiK
Plasmid carrying yggA: pMW118::yggA Example 2

Effect of Amplification of the yahN, yeaS, yfiK, and yggA DNA Fragments on the E. coli TG1 Resistance to Some Amino Acids and Amino Acid Analogues The homology of the yeaS, yfiK, yahN, and yggA gene products with the lysine transporter, LysE, of Corynebacterium glutamicum (Vrljic et al., Mol. Microbiol., 22, 815-826, 1996) and RhtB protein involved in homoserine excretion, indicates functional analogues for these proteins. It is well known that the increased expression of genes involved in antibiotic and heavy metal efflux increases the level of resistance to the drugs (Nikaido, H. J. Bacteriology, 178, 5853-5859, 1996). Therefore, the effect of the pYEAS, pYAHN, pYFIK, and pYGGA plasmids on susceptibility of the strain TG1 to some amino acids and amino acid analogues was tested. Overnight cultures of the E. coli strains TG1/pYEAS, TG1/pYAHN, TG1/pYFIK, TG1/pYGGA and of the control strains TG1/pUC21, TG1/pUC19 and TG1/pOK12 grown in M9 minimal medium with an appropriate antibiotic on a rotary shaker ($10^9$ cfu/ml) were diluted 1:100 in M9 minimal medium and grown for 5 h in the same medium. Then the log phase cultures thus obtained were diluted and about $10^4$ live cells were applied to well-dried test plates with M9 agar containing doubling increments of amino acids or analogues. Thus, the minimum inhibition concentration (MIC) of these compounds was examined.

The results are shown in Table 1. It follows from the Table 1 that multiple copies of the yfiK gene conferred increased resistance to proline, homoserine, histidine, threonine, glutamate, lysine, α-amino-β-hydroxyvaleric-acid (AHVA), S-(2-aminoethyl)-L-cysteine (AEC), and α-aminobutyric acid; multiple copies of yahN gene conferred increased resistance to proline, multiple copies of the yeaS gene conferred increased resistance to threonine, homoserine, lysine, glutamate, histidine, proline, and α-aminobutyric acid; multiple copies of yggA gene conferred increased resistance to S-(2-aminoethyl)-L-cysteine (AEC), lysine, and arginine. These results indicate that except for YahN, all of the presumed transporters have specificity to several substrates (amino acids and amino acid analogues), or may show non-specific effects as a result of amplification.

TABLE 1

| Substrate | MIC (μg/ml) for E. coli TG1, harboring the plasmid | | | | |
| --- | --- | --- | --- | --- | --- |
| | pUC21 | pYFIK | pYAHN | pYEAS | pYGGA |
| L-homoserine | 500 | 1000 | 500 | 1000 | 500 |
| L-threonine | 30000 | 40000 | 30000 | 50000 | 30000 |
| L-lysine | 5000 | 7500 | 5000 | 7500 | 15000 |
| L-glutamate (Na salt) | 5000 | 10000 | 5000 | 20000 | 5000 |
| L-histidine | 5000 | 10000 | 5000 | 30000 | 5000 |
| L-valine | 0.5 | 0.5 | 0.5 | 0.5 | 0.5 |
| L-proline | 1000 | 5000 | 2000 | 2000 | 1000 |
| L-arginine | 10000 | 10000 | 10000 | 10000 | 20000 |
| AHVA | 100 | 200 | 100 | 100 | 100 |
| AEC | 5 | 10 | 5 | 5 | 200 |

TABLE 1-continued

| | MIC (µg/ml) for E. coli TG1, harboring the plasmid | | | | |
|---|---|---|---|---|---|
| Substrate | pUC21 | pYFIK | pYAHN | pYEAS | pYGGA |
| α-aminobutyric acid | 2500 | 5000 | 2500 | >10000 | 2500 |
| 4-aza-DL-leucine | 100 | 100 | 100 | 100 | 100 |

Example 3

Effect of Amplification of the yeas, yahN, and yfiK DNA Fragments on Glutamic Acid Production The *E. coli* strain AJ13199 (FR patent No. 2747689) was transformed with the vector pUC21 and each of the plasmids pYAHN, pYEAS and pYFIK. Thus the strains AJ13199/pUC21 (VKPM B-7728), AJ13199/pYAHN (VKPM B-7729), AJ13199/pYEAS (VKPM B-7731), and AJ13199/pYFIK (VKPM B-7730) were obtained.

These strains were each cultivated at 37° C. for 18 hours in a nutrient broth with 100 mg/l ampicillin, and 0.3 ml of the obtained culture was inoculated into 3 ml of a fermentation medium containing 100 mg/l ampicillin, in a 20×200 mm test tube, and cultivated at 37° C. for 48 hours on a rotary shaker. After the cultivation, the amount of glutamic acid which had accumulated in the medium was determined by a known method.

The composition of the fermentation medium (g/l):

| | |
|---|---|
| Glucose | 80 |
| $(NH_4)_2SO_4$ | 22 |
| $K_2HPO_4$ | 2 |
| NaCl | 0.8 |
| $MgSO_4 \cdot 7H_2O$ | 0.8 |
| $FeSO_4 \cdot 7H_2O$ | 0.02 |
| $MnSO_4 \cdot 5H_2O$ | 0.02 |
| Thiamine HCl | 0.0002 |
| Yeast extract | 1.0 |
| $CaCO_3$ | 30.0 (dry-heat-sterilized at 180° C. for 2 h) |

(Glucose and $K_2HPO_4$ separately sterilized)

The results are shown in Table 2. As shown in Table 2, the strains AJ13199/pYAHN, AJ13199/pYEAS, and AJ13199/pYFIK yielded glutamic acid in a larger amount than the strain AJ13199/pUC21, in which expression of amino acid excretion proteins was not enhanced.

TABLE 2

| Strain | Glutamic acid, g/l |
|---|---|
| AJ13199/pUC21 | 21.9 |
| AJ13199/pYAHN | 27.9 |
| AJ13199/pYEAS | 29.7 |
| AJ13199/pYFIK | 28.4 |

Example 4

Effect of Amplification of yeaS, yahN, and yfiK DNA Fragments on Lysine Production (1) As the lysine-producing bacterium belonging to the genus *Escherichia*, *E. coli* strain W3110 (TyrA) described in European Patent Publication No. 488424, and which contains plasmid pCABD2, described in International Publication No. WO 95/16042, was used. Specifically, plasmid pCABD2, and each of the plasmid pMW118::yahN, pMW118::yeaS, pMW118::yfiK and pMW118 were introduced into *E. coli* strain W3110 (TyrA) to obtain the following strains:
W3110 (tyrA)/pCABD2+pMW118::yahN
W3110 (tyrA)/pCABD2+pMW118::yeaS
W3110 (tyrA)/pCABD2+pMW118::yfik
W3110 (tyrA)/pCABD2+pMW118.

Lysine productivity of these strains was estimated by culturing. The composition of the medium was as follows (g/l):

| | |
|---|---|
| Glucose | 40.0 |
| $MgSO_4 \cdot 7H_2O$ | 1.0 |
| $(NH_4)_2SO_4$ | 16.0 |
| $K_2HPO_4$ | 1.0 |
| $FeSO_4 \cdot 7H_2O$ | 0.01 |
| $MnSO_4 \cdot 7H_2O$ | 0.01 |
| Yeast extract (Difco) | 2.0 |
| Tyrosine | 0.1 |
| Adjusted to pH 7.0 and autoclaved at 115° C. for 10 minutes. (Glucose and $MgSO_4 \cdot 7H_2O$ separately sterilized) | |
| Pharmacopeial $CaCO_3$ | 25 g/l (dry-heat-sterilized at 180° C. for 2 h) |

Adjusted to pH 7.0 and autoclaved at 115° C. for 10 minutes. Glucose and $MgSO_4. 7H_2O$ separately sterilized)

Pharmacopeial $CaCO_3$ 25 g/l (dry-heat-sterilized at 180° C. for 2 h)

As antibiotics, 20 mg/l of streptomycin and 50 mg/l of ampicillin were added depending on the plasmid. Cultivation was conducted at 37° C. for 30 hours with agitation at 115 rpm. The results are shown in Table 3.

TABLE 3

| Strain | Lysine, g/l | Yield, (%) |
|---|---|---|
| W3110(tyrA) | 0.08 | 0.2 |
| W3110(tyrA)/pCABD2 + pMW118 | 12.2 | 30.5 |
| W3110(tyrA)/pCABD2 + pMW118::yahN | 13.8 | 34.5 |
| W3110(tyrA)/pCABD2 + pMW118::yeaS | 12.7 | 31.8 |
| W3110(tyrA)/pCABD2 + pMW118::yfiK | 12.2 | 30.5 |

Table 3 shows that the amount produced and the yield based on consumed sugar of lysine is increased by enhancing YahN and YeaS.

(2) As the lysine-producing bacterium belonging to the genus *Escherichia*, *E. coli* strain VL614 was used. This strain is a derivative of the known *E. coli* strain VL613 (SU Patent No. 1354458). In turn, the strain VL613 was obtained from the known strain Gif102 (Theze, J. and Saint Girons. J. Bacteriol., 118, 990-998, 1974) in the three steps:

In the first step, the mutants resistant to 2 mg/ml S-(2-aminoethyl)-L-cysteine were selected, and among them strain VL611 was found able to produce L-lysine.

In the second step, the genes involved in sucrose utilization and located on the transposon Tn2555 (Doroshenko et al., Mol. Biologiya, 22, 645-658, 1988), were introduced into VL611 using phage P1-mediated transduction giving the strain VL612.

In the third step, the mutation rhtA23 from the strain VKPM B-3996, conferring resistance to threonine and homoserine (U.S. Pat. No. 5,175,107) was introduced into VL612 by phage P1 transduction giving the strain VL613.

The *E. coli* strain VL614 was obtained by transduction of the wild-type allele of the rhtA gene from the *E. coli* strain VKPM B-6204 (MG1655 zbi3058::Tn10) to VL613. Transductants were selected on L-medium containing 10 mg/l tetracyclin, and among them the strain VL614 (rhtA⁺) sensitive to 10 g/l homoserine was found.

The strain VL614 was transformed with the pYGGA plasmid or with the pOK12 vector to obtain strains VL614/pYGGA (VKPM B-7719) and VL614/pOK12 (VKPM B-7722).

These strains were each cultivated at 37° C. for 18 hours in a nutrient broth with 50 mg/l kanamycin, and 0.3 ml of the obtained culture was inoculated into 3 ml of a fermentation medium (Example 3) containing 0.3 μl threonine, 0.3 μl methionine and 50 mg/l kanamycin, in a 20×200 mm test tube, and cultivated at 37° C. for 48 hours on a rotary shaker. After the cultivation, the amount of lysine and glutamate which accumulated in the medium was each determined by a known method.

The results are shown in Table 4.

TABLE 4

| Strain | Lysine, g/l | Glutamate, g/l |
|---|---|---|
| VL614/pOK12 | 2.6 | 0.8 |
| VL614/pYGGA | 3.6 | 2.2 |

As shown in Table 4, the strain VL614/pYGGA yielded lysine in a larger amount than the strain VL614/pOK12, in which the yggA gene was not enhanced. Besides, the strain VL614/pYGGA yielded more glutamic acid than the strain VL614/pOK12.

Example 5

Effect of Amplification of yeaS, yahN, and yfiK DNA Fragments on Threonine, Alanine, Valine, and Isoleucine Production As the threonine-producing bacterium belonging to the genus *Escherichia*, the *E. coli* strain VL2054 was used. This strain was derived from the known *E. coli* strain VKPM B-3996 (U.S. Pat. No. 5,175,107) as follows.

Initially, a new recipient strain was constructed in several steps:

The plasmidless derivative of the strain VKPM B-3996 was selected after spontaneous elimination of pVIC40 plasmid.

The wild-type allele of the rhtA gene from the *E. coli* strain VKPM B-6204 (MG1655 zbi3058::Tn10) was introduced into the thus obtained strain by phage P1 mediated transduction as in the Example 4.

A mutation inactivating kan gene of the Tn5 transposon inserted into the tdh gene was obtained after NG mutagenesis and selection of kanamycin-sensitive cells still unable to degrade threonine. Thus the strain VL2053 was obtained.

On the other hand, the threonine operon from pVIC40 was cloned into integrative Mud vector under the $P_R$ promoter of the phage lambda. In addition, the cat gene of Tn9 conferring the resistance to chloramphenicol was cloned into the same vector. The construct thus obtained was inserted into the chromosome of the *E. coli* strain C600 by use of a known method (U.S. Pat. No. 5,595,889) and transduced from the thus obtained strain to VL2053, giving the new plasmidless threonine-producing strain VL2054. This strain was able to yield alanine, valine and isoleucine in the culture broth.

The strain VL2054 was transformed with each of the plasmids pYEAS, pYFIK, and with the vector pUC21 to obtain *E. coli* strains VL2054/pYEAS (VKPM B-7707), VL2054/pYFIK (VKPM B-7712), and VL2054/pUC21 (VKPM B-7708).

These strains were each cultivated at 37° C. for 18 hours in a nutrient broth with 100 mg/l ampicillin, and 0.3 ml of the obtained culture was inoculated into 3 ml of a fermentation medium (Example 3) containing 100 mg/l ampicillin, in a 20×200 mm test tube, and cultivated at 37° C. for 48 hours with a rotary shaker. After the cultivation, threonine, alanine, valine and isoleucine each accumulated in the medium, and the amount of each was determined by a known method.

The results are shown in Table 5.

As shown in Table 5, the strain VL2054/pYFIK yielded threonine in a larger amount than the strain VL2054/pUC21 in which the yfiK gene was not enhanced. Besides, the strain VL2054/pYEAS yielded more alanine, valine, and isoleucine than the strain VL2054/pUC21, in which the yeaS gene was not enhanced.

TABLE 5

| Strain | Amino acid accumulation, g/l | | | |
|---|---|---|---|---|
| | Threonine | Alanine | Valine | Isoleucine |
| VL2054/pUC21 | 5.8 | 0.4 | 0.31 | 0.15 |
| VL2054/pYEAS | 5.2 | 1.4 | 0.52 | 0.45 |
| VL2054/pYFIK | 8.8 | 0.5 | 0.22 | 0.14 |

Example 6

Effect of Amplification of yeaS and yfiK DNA Fragments on Histidine Production

As the histidine-producing bacterium belonging to the genus *Escherichia*, the strain *E. coli* VL2160 was used. This strain was obtained based on the known strain NK5526 hisG::Tn10 (VKPM B-3384) by phage P1-mediated transduction of the hisG$^R$ mutation desensitizing ATP-phosphoribosyltransferase from the strain CC46 (Astvatsaturianz et al., Genetika, 24, 1928-1934, 1988). The strain *E. coli* VL2160 was transformed with each of the plasmids pYEAS, pYFIK, and with the vectors pUC21 to obtain *E. coli* strains VL2160/pYEAS (VKPM B-7753), *E. coli* VL2160/pYFIK (VKPM B-7754), *E. coli* VL2160/pUC21 (VKPM B-7752).

These strains were each cultivated at 37° C. for 18 hours in a nutrient broth with 100 mg/l ampicillin, and 0.3 ml of the obtained culture was inoculated into 3 ml of the fermentation medium (Example 3) containing an increased amount of yeast extract (3 g/l) and 100 mg/l ampicillin, in a 20×200 mm test tube, and cultivated at 34° C. for 68 hours on a rotary shaker.

After the cultivation, the amount of histidine which had accumulated in the medium was determined by a known method. The results are shown in Table 6.

TABLE 6

| Strain | Histidine, g/l |
|---|---|
| VL2160/pUC21 | 1.2 |
| VL2160/pYEAS | 1.8 |
| VL2160/pYFIK | 1.4 |

As shown in Table 6, the strains E. coli VL2160/pYEAS and E. coli VL2160/pYFIK yielded histidine in a larger amount than the strain E. coli VL2160/pUC21, in which the yeaS and yfiK genes were not enhanced.

Example 7

Effect of Amplification of yahN, yfiK and yeaS DNA Fragments on Proline Production As the proline-producing bacterium belonging to the genus Escherichia, the strain VL2151 (W3350 proB* ΔputAP Tn10) was used. This strain was obtained by transduction into W3350 of ΔputAP mutation linked to Tn10 and selecting tetracycline-resistant transductants unable to utilize proline as a sole carbon source. The thus obtained strain W3350 ΔputAP Tn10 was mutagenized with NG and mutants resistant to 20 mg/l of 3,4-dehydro-DL-proline were selected. Among them the strain VL2151 (W3350 proB* ΔputAP Tn10) was found able to produce proline.

The strain E. coli VL2151 was transformed with each of the plasmids pYEAS, pYFIK, pYAHN and with the vector pUC21 to obtain E. coli strains VL2151/pYEAS (VKPM B-7714), VL2151/pYFIK (VKPM B-7713), VL2151/pYAHN (VKPM B-7748) and E. coli VL2151/pUC21 (VKPM B-7715).

These strains were each cultivated at 37° C. for 18 hours in a nutrient broth with 100 mg/l ampicillin, and 0.3 ml of the obtained culture was inoculated into 3 ml of a fermentation medium (Example 3) containing 100 mg/l ampicillin, in a 20×200 mm test tube, and cultivated at 37° C. for 48 hours on a rotary shaker. After the cultivation, the amount of proline which had accumulated in the medium was determined by a known method. The results are shown in Table 7.

TABLE 7

| Strain | Proline, g/l |
| --- | --- |
| VL2151/pUC21 | 1.8 |
| VL2151/pYAHN | 2.2 |
| VL2151/pYEAS | 2.1 |
| VL2151/pYFIK | 2.5 |

As shown in Table 7, the strains E. coli VL2151/pYFIK, E. coli VL2151/pYAHN and E. coli VL2151/pYEAS yielded proline in a larger amount than the strain E. coli VL2151/pUC21, in which the yfiK, yahN and yeaS genes were not enhanced. The amplification of the yfiK gene had the most pronounced effect.

Example 8

Effect of Amplification of yggA DNA Fragments on Arginine Production

As arginine-producing bacterium belonging to the genus Escherichia, the strain W3350 argE::Tn10/pKA10 was used. This strain harbors a plasmid, pKA10, which contains a DNA region from Corynebacterium (Brevibacterium) flavum which complements at least argA and argE mutations in the recipient strain of E. coli K-12 (Kharitonov A. and Tarasov A. P. Molecular Genetics, Microbiology and Virology. No. 9, 29-33, 1986).

The strain E. coli W3350 argE::Tn10/pKA10 was transformed with the plasmid pYGGA, or with the vector pOK12 to obtain the strains E. coli W3350 argE::Tn10/pKA10, pYGGA (VKPM B-7716) and E. coli W3350 argE::Tn10/pKA10, pOK12 (VKPM B-7718).

The thus obtained transformants were each cultivated at 37° C. for 18 hours in a nutrient broth with 100 mg/l ampicillin and 50 mg/l kanamycin, and 0.3 ml of the obtained culture was inoculated into 3 ml of a fermentation medium (Example 3) containing 100 mg/l ampicillin and 50 mg/l kanamycin, in a 20×200 mm test tube, and cultivated at 37° C. for 48 hours on a rotary shaker. After the cultivation, the amount of arginine which had accumulated in the medium was determined by a known method.

The results are shown in Table 8.

TABLE 8

| Strain | Arginine, g/l |
| --- | --- |
| W3350 argE::Tn10/pKA10, pOK12 | 0.11 |
| W3350 argE::Tn10/pKA10, pYGGA | 0.46 |

As shown in Table 8, the strains E. coli W3350 argE::Tn10/pKA10, pYGGA yielded arginine in a larger amount than the strain E. coli W3350 argE::Tn10/pKA10, pUC21 in which the yggA gene was not enhanced.

The following E. coli strains have been deposited according to the Budapest Treaty in the Russian National Collection of Industrial Microorganisms (VKPM) on Dec. 29, 1998 under the accession numbers shown in parenthesis.

AJ13199/pUC21 VKPM B-7728)
AJ13199/pYAHN (VKPM B-7729)
AJ13199/pYEAS (VKPM B-7731)
AJ13199/pYFIK (VKPM B-7730)
VL614/pYGGA (VKPM B-7719)
VL614/pOK12 (VKPM B-7722)
VL2054/pYEAS (VKPM B-7707)
VL2054/pYFIK (VKPM B-7712)
VL2054/pUC21 (VKPM B-7708)
VL2160/pYEAS (VKPM B-7753)
VL2160/pYFIK (VKPM B-7754)
VL2160/pUC21 (VKPM B-7752)
VL2151/pYFIK (VKPM B-7713)
VL2151/pYEAS (VKPM B-7714)
VL2151/pYAHN (VKPM B-7748)
VL2151/pUC21 (VKPM B-7715)
W3350 argE::Tn10/pKA10, pYGGA (VKPM B-7716)
W3350 argE::Tn10/pKA10, pOK12 (VKPM B-7718)

While the invention has been described in detail with reference to preferred embodiments thereof, it will be apparent to one skilled in the art that various changes can be made, and equivalents employed, without departing from the scope of the invention. Each of the aforementioned documents, including the foreign priority document, is incorporated by reference herein in its entirety.

We claim:

1. A method for producing an L-amino acid selected from the group consisting of L-glutamic acid, L-threonine, L-histidine, and L-proline comprising:
   I) cultivating in a culture medium an *Escherichia* bacterium which has an ability to produce an L-amino acid selected from the group consisting of L-glutamic acid, L-threonine, L-histidine, and L-proline, wherein said ability to produce the L-amino acid is increased by increasing expression of a protein comprising an amino acid sequence shown in SEQ ID NO: 14, wherein the expression is increased relative to the expression of said protein in a wild-type *Escherichia* bacterium by increasing the copy number of the DNA coding for said protein or by replacing the native promoter with a stronger promoter for expression of the DNA coding for said protein, and
   II) recovering the L-amino acid from the medium.

2. The method according to claim 1, wherein said L-amino acid is L-glutamic acid.

3. The method according to claim 1, wherein said L-amino acid is L-threonine.

4. The method according to claim 1, wherein said L-amino acid is L-histidine.

5. The method according to claim 1, wherein said L-amino acid is L-proline.

6. The method according to claim 1, wherein the copy number of a DNA coding for said protein in said bacterium is increased.

7. The method according to claim 6, wherein said DNA is located on a multicopy vector.

8. The method according to claim 6, wherein said DNA is located on a transposon.

* * * * *

SEQUENCE LISTING

<160> NUMBER OF SEQ ID NOS: 24

<210> SEQ ID NO 1
<211> LENGTH: 27
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 1
ggcgagctcc cagtaaccgg aaataag                                          27

<210> SEQ ID NO 2
<211> LENGTH: 27
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 2
cgctctagaa aggaccacgc attacgg                                          27

<210> SEQ ID NO 3
<211> LENGTH: 27
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 3
ggcgagctca gattggttag catattc                                          27

<210> SEQ ID NO 4
<211> LENGTH: 27
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 4
cggtctagaa tcagcgaaga atcaggg                                          27

<210> SEQ ID NO 5
<211> LENGTH: 27
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 5
ggcgagctca tgttccgtgt cgggtac                                          27

<210> SEQ ID NO 6
<211> LENGTH: 27
<212> TYPE: DNA
<213> ORGANISM: Artificial Sequence
<220> FEATURE:
<221> NAME/KEY: misc_feature
<223> OTHER INFORMATION: Description of Artificial Sequence: synthetic DNA

<400> SEQUENCE: 6
ggctctagat agcaagttac taagcgg       27

<210> SEQ ID NO 7
<211> LENGTH: 35
<212> TYPE: DNA
<213> ORGANISM: Artificial Sequence
<220> FEATURE:
<221> NAME/KEY: misc_feature
<223> OTHER INFORMATION: Description of Artificial Sequence: synthetic DNA

<400> SEQUENCE: 7
ctctgaattc tctcttatta gttttctga ttgcc       35

<210> SEQ ID NO 8
<211> LENGTH: 38
<212> TYPE: DNA
<213> ORGANISM: Artificial Sequence
<220> FEATURE:
<221> NAME/KEY: misc_feature
<223> OTHER INFORMATION: Description of Artificial Sequence: synthetic DNA

<400> SEQUENCE: 8
cgtgacctgc agcgttctca cagcgcggta gcctttaa       38

<210> SEQ ID NO 9
<211> LENGTH: 672
<212> TYPE: DNA
<213> ORGANISM: Escherichia coli
<220> FEATURE:
<221> NAME/KEY: CDS
<222> LOCATION: (1)..(672)

<400> SEQUENCE: 9

```
atg atg cag tta gtt cac tta ttt atg gat gaa atc act atg gat cct    48
Met Met Gln Leu Val His Leu Phe Met Asp Glu Ile Thr Met Asp Pro
1               5                  10                  15 ttg cat gcc gtt tac ctg acc gta gga ctg ttc gtg att act ttt ttt    96
Leu His Ala Val Tyr Leu Thr Val Gly Leu Phe Val Ile Thr Phe Phe
            20                  25                  30 aat ccg gga gcc aat ctc ttt gtg gta gta caa acc agc ctg gct tcc   144
Asn Pro Gly Ala Asn Leu Phe Val Val Val Gln Thr Ser Leu Ala Ser
        35                  40                  45 ggt cga cgc gca ggg gtg ctg acc ggg ctg ggc gtg gcg ctg ggc gat   192
Gly Arg Arg Ala Gly Val Leu Thr Gly Leu Gly Val Ala Leu Gly Asp
    50                  55                  60 gca ttt tat tcc ggg ttg ggt ttg ttt ggt ctt gca acg cta att acg   240
Ala Phe Tyr Ser Gly Leu Gly Leu Phe Gly Leu Ala Thr Leu Ile Thr
65                  70                  75                  80 cag tgt gag gag att ttt tcg ctt atc aga atc gtc ggc ggc gct tat   288
Gln Cys Glu Glu Ile Phe Ser Leu Ile Arg Ile Val Gly Gly Ala Tyr
                85                  90                  95 ctc tta tgg ttt gcg tgg tgc agc atg cgc cgc cag tca aca ccg caa   336
Leu Leu Trp Phe Ala Trp Cys Ser Met Arg Arg Gln Ser Thr Pro Gln
            100                 105                 110 atg agc aca cta caa caa ccg att agc gcc ccc tgg tat gtc ttt ttt   384
Met Ser Thr Leu Gln Gln Pro Ile Ser Ala Pro Trp Tyr Val Phe Phe
        115                 120                 125
```

```
cgc cgc gga tta att acc gat ctc tct aac ccg caa acc gtt tta ttt     432
Arg Arg Gly Leu Ile Thr Asp Leu Ser Asn Pro Gln Thr Val Leu Phe
        130                 135                 140 ttt atc agt att ttc tca gta aca tta aat gcc gaa aca cca aca tgg     480
Phe Ile Ser Ile Phe Ser Val Thr Leu Asn Ala Glu Thr Pro Thr Trp
145                 150                 155                 160 gca cgt tta atg gcc tgg gcg ggg att gtg ctc gca tca att atc tgg     528
Ala Arg Leu Met Ala Trp Ala Gly Ile Val Leu Ala Ser Ile Ile Trp
                165                 170                 175 cga gtt ttt ctt agt cag gcg ttt tct ttg ccc gct gtg cgt cgt gct     576
Arg Val Phe Leu Ser Gln Ala Phe Ser Leu Pro Ala Val Arg Arg Ala
            180                 185                 190 tat ggg cgt atg caa cgc gtt gcc agt cgg gtt att ggt gca att att     624
Tyr Gly Arg Met Gln Arg Val Ala Ser Arg Val Ile Gly Ala Ile Ile
        195                 200                 205 ggt gta ttc gcg cta cgc ctg att tac gaa ggg gtg acg cag cgg tga     672
Gly Val Phe Ala Leu Arg Leu Ile Tyr Glu Gly Val Thr Gln Arg
    210                 215                 220

<210> SEQ ID NO 10
<211> LENGTH: 223
<212> TYPE: PRT
<213> ORGANISM: Escherichia coli

<400> SEQUENCE: 10

Met Met Gln Leu Val His Leu Phe Met Asp Glu Ile Thr Met Asp Pro
1               5                   10                  15

Leu His Ala Val Tyr Leu Thr Val Gly Leu Phe Val Ile Thr Phe Phe
                20                  25                  30

Asn Pro Gly Ala Asn Leu Phe Val Val Gln Thr Ser Leu Ala Ser
            35                  40                  45

Gly Arg Arg Ala Gly Val Leu Thr Gly Leu Gly Val Ala Leu Gly Asp
        50                  55                  60

Ala Phe Tyr Ser Gly Leu Gly Leu Phe Gly Leu Ala Thr Leu Ile Thr
65                  70                  75                  80

Gln Cys Glu Glu Ile Phe Ser Leu Ile Arg Ile Val Gly Gly Ala Tyr
                85                  90                  95

Leu Leu Trp Phe Ala Trp Cys Ser Met Arg Arg Gln Ser Thr Pro Gln
            100                 105                 110

Met Ser Thr Leu Gln Gln Pro Ile Ser Ala Pro Trp Tyr Val Phe Phe
        115                 120                 125

Arg Arg Gly Leu Ile Thr Asp Leu Ser Asn Pro Gln Thr Val Leu Phe
    130                 135                 140

Phe Ile Ser Ile Phe Ser Val Thr Leu Asn Ala Glu Thr Pro Thr Trp
145                 150                 155                 160

Ala Arg Leu Met Ala Trp Ala Gly Ile Val Leu Ala Ser Ile Ile Trp
                165                 170                 175

Arg Val Phe Leu Ser Gln Ala Phe Ser Leu Pro Ala Val Arg Arg Ala
            180                 185                 190

Tyr Gly Arg Met Gln Arg Val Ala Ser Arg Val Ile Gly Ala Ile Ile
        195                 200                 205

Gly Val Phe Ala Leu Arg Leu Ile Tyr Glu Gly Val Thr Gln Arg
    210                 215                 220

<210> SEQ ID NO 11
<211> LENGTH: 639
<212> TYPE: DNA
```

<213> ORGANISM: Escherichia coli
<220> FEATURE:
<221> NAME/KEY: CDS
<222> LOCATION: (1)..(639)

<400> SEQUENCE: 11

```
gtg ttc gct gaa tac ggg gtt ctg aat tac tgg acc tat ctg gtt ggg      48
Val Phe Ala Glu Tyr Gly Val Leu Asn Tyr Trp Thr Tyr Leu Val Gly
 1               5                  10                  15 gcc att ttt att gtg ttg gtg cca ggg cca aat acc ctg ttt gta ctc      96
Ala Ile Phe Ile Val Leu Val Pro Gly Pro Asn Thr Leu Phe Val Leu
             20                  25                  30 aaa aat agc gtc agt agc ggt atg aaa ggc ggt tat ctt gcg gcc tgc     144
Lys Asn Ser Val Ser Ser Gly Met Lys Gly Gly Tyr Leu Ala Ala Cys
         35                  40                  45 ggt gta ttt att ggc gat gcg gta ttg atg ttt ctg gca tgg gct gga     192
Gly Val Phe Ile Gly Asp Ala Val Leu Met Phe Leu Ala Trp Ala Gly
     50                  55                  60 gtg gcg aca tta att aag acc acc ccg ata tta ttc aac att gta cgt     240
Val Ala Thr Leu Ile Lys Thr Thr Pro Ile Leu Phe Asn Ile Val Arg
 65                  70                  75                  80 tat ctt ggt gcg ttt tat ttg ctc tat ctg ggg agt aaa att ctt tac     288
Tyr Leu Gly Ala Phe Tyr Leu Leu Tyr Leu Gly Ser Lys Ile Leu Tyr
                 85                  90                  95 gcg acc ctg aag ggt aaa aat agc gag gcc aaa tcc gat gag ccc caa     336
Ala Thr Leu Lys Gly Lys Asn Ser Glu Ala Lys Ser Asp Glu Pro Gln
            100                 105                 110 tac ggt gct att ttt aaa cgc gcg tta att ttg agc ctg act aat ccg     384
Tyr Gly Ala Ile Phe Lys Arg Ala Leu Ile Leu Ser Leu Thr Asn Pro
        115                 120                 125 aaa gcc att ttg ttc tat gtg tcg ttt ttc gta cag ttt atc gat gtt     432
Lys Ala Ile Leu Phe Tyr Val Ser Phe Phe Val Gln Phe Ile Asp Val
    130                 135                 140 aat gcc cca cat acg gga att tca ttc ttt att ctg gcg gcg acg ctg     480
Asn Ala Pro His Thr Gly Ile Ser Phe Phe Ile Leu Ala Ala Thr Leu
145                 150                 155                 160 gaa ctg gtg agt ttc tgc tat ttg agc ttc ctg att ata tct ggt gct     528
Glu Leu Val Ser Phe Cys Tyr Leu Ser Phe Leu Ile Ile Ser Gly Ala
                165                 170                 175 ttt gtc acg cag tac ata cgt acc aaa aag aaa ctg gct aaa gtt ggc     576
Phe Val Thr Gln Tyr Ile Arg Thr Lys Lys Lys Leu Ala Lys Val Gly
            180                 185                 190 aac tca ctg att ggt ttg atg ttc gtg ggt ttc gct gcc cga ctg gcg     624
Asn Ser Leu Ile Gly Leu Met Phe Val Gly Phe Ala Ala Arg Leu Ala
        195                 200                 205 acg ctg caa tcc tga                                                  639
Thr Leu Gln Ser
    210
```

<210> SEQ ID NO 12
<211> LENGTH: 212
<212> TYPE: PRT
<213> ORGANISM: Escherichia coli

<400> SEQUENCE: 12

```
Val Phe Ala Glu Tyr Gly Val Leu Asn Tyr Trp Thr Tyr Leu Val Gly
 1               5                  10                  15

Ala Ile Phe Ile Val Leu Val Pro Gly Pro Asn Thr Leu Phe Val Leu
             20                  25                  30

Lys Asn Ser Val Ser Ser Gly Met Lys Gly Gly Tyr Leu Ala Ala Cys
         35                  40                  45
```

```
Gly Val Phe Ile Gly Asp Ala Val Leu Met Phe Leu Ala Trp Ala Gly
    50                  55                  60

Val Ala Thr Leu Ile Lys Thr Thr Pro Ile Leu Phe Asn Ile Val Arg
65                  70                  75                  80

Tyr Leu Gly Ala Phe Tyr Leu Leu Tyr Leu Gly Ser Lys Ile Leu Tyr
                85                  90                  95

Ala Thr Leu Lys Gly Lys Asn Ser Glu Ala Lys Ser Asp Glu Pro Gln
            100                 105                 110

Tyr Gly Ala Ile Phe Lys Arg Ala Leu Ile Leu Ser Leu Thr Asn Pro
        115                 120                 125

Lys Ala Ile Leu Phe Tyr Val Ser Phe Phe Val Gln Phe Ile Asp Val
    130                 135                 140

Asn Ala Pro His Thr Gly Ile Ser Phe Phe Ile Leu Ala Ala Thr Leu
145                 150                 155                 160

Glu Leu Val Ser Phe Cys Tyr Leu Ser Phe Leu Ile Ile Ser Gly Ala
                165                 170                 175

Phe Val Thr Gln Tyr Ile Arg Thr Lys Lys Lys Leu Ala Lys Val Gly
            180                 185                 190

Asn Ser Leu Ile Gly Leu Met Phe Val Gly Phe Ala Ala Arg Leu Ala
        195                 200                 205

Thr Leu Gln Ser
    210

<210> SEQ ID NO 13
<211> LENGTH: 588
<212> TYPE: DNA
<213> ORGANISM: Escherichia coli
<220> FEATURE:
<221> NAME/KEY: CDS
<222> LOCATION: (1)..(588)

<400> SEQUENCE: 13 gtg aca ccg acc ctt tta agt gct ttt tgg act tac acc ctg att acc      48
Val Thr Pro Thr Leu Leu Ser Ala Phe Trp Thr Tyr Thr Leu Ile Thr
1               5                   10                  15 gct atg acg cca gga ccg aac aat att ctc gcc ctt agc tct gct acg      96
Ala Met Thr Pro Gly Pro Asn Asn Ile Leu Ala Leu Ser Ser Ala Thr
            20                  25                  30 tcg cat gga ttt cgt caa agt acc cgc gtg ctg gca ggg atg agt ctg     144
Ser His Gly Phe Arg Gln Ser Thr Arg Val Leu Ala Gly Met Ser Leu
        35                  40                  45 gga ttt ttg att gtg atg tta ctg tgt gcg ggc att tca ttt tca ctg     192
Gly Phe Leu Ile Val Met Leu Leu Cys Ala Gly Ile Ser Phe Ser Leu
    50                  55                  60 gca gtg att gac ccg gca gcg gta cac ctt ttg agt tgg gcg ggg gcg     240
Ala Val Ile Asp Pro Ala Ala Val His Leu Leu Ser Trp Ala Gly Ala
65                  70                  75                  80 gca tat att gtc tgg ctg gcg tgg aaa atc gcc acc agc cca aca aag     288
Ala Tyr Ile Val Trp Leu Ala Trp Lys Ile Ala Thr Ser Pro Thr Lys
                85                  90                  95 gaa gac gga ctt cag gca aaa cca atc agc ttt tgg gcc agc ttt gct     336
Glu Asp Gly Leu Gln Ala Lys Pro Ile Ser Phe Trp Ala Ser Phe Ala
            100                 105                 110 ttg cag ttt gtg aac gtc aaa atc att ttg tac ggt gtt acg gca ctg     384
Leu Gln Phe Val Asn Val Lys Ile Ile Leu Tyr Gly Val Thr Ala Leu
        115                 120                 125 tcg acg ttt gtt ctg ccg caa aca cag gcg tta agc tgg gta gtt ggc     432
Ser Thr Phe Val Leu Pro Gln Thr Gln Ala Leu Ser Trp Val Val Gly
```

```
            130                 135                 140
gtc agc gtt ttg ctg gcg atg att ggg acg ttt ggc aat gtg tgc tgg    480
Val Ser Val Leu Leu Ala Met Ile Gly Thr Phe Gly Asn Val Cys Trp
145                 150                 155                 160 gcg ctg gcg ggg cat ctg ttt cag cga ttg ttt cgc cag tat ggt cgc    528
Ala Leu Ala Gly His Leu Phe Gln Arg Leu Phe Arg Gln Tyr Gly Arg
                165                 170                 175 cag tta aat atc gtg ctt gcc ctg ttg ctg gtc tat tgc gcg gta cgc    576
Gln Leu Asn Ile Val Leu Ala Leu Leu Leu Val Tyr Cys Ala Val Arg
            180                 185                 190 att ttc tat taa                                                    588
Ile Phe Tyr
        195

<210> SEQ ID NO 14
<211> LENGTH: 195
<212> TYPE: PRT
<213> ORGANISM: Escherichia coli

<400> SEQUENCE: 14

Val Thr Pro Thr Leu Leu Ser Ala Phe Trp Thr Tyr Thr Leu Ile Thr
1               5                   10                  15

Ala Met Thr Pro Gly Pro Asn Asn Ile Leu Ala Leu Ser Ser Ala Thr
            20                  25                  30

Ser His Gly Phe Arg Gln Ser Thr Arg Val Leu Ala Gly Met Ser Leu
        35                  40                  45

Gly Phe Leu Ile Val Met Leu Leu Cys Ala Gly Ile Ser Phe Ser Leu
    50                  55                  60

Ala Val Ile Asp Pro Ala Ala Val His Leu Leu Ser Trp Ala Gly Ala
65                  70                  75                  80

Ala Tyr Ile Val Trp Leu Ala Trp Lys Ile Ala Thr Ser Pro Thr Lys
                85                  90                  95

Glu Asp Gly Leu Gln Ala Lys Pro Ile Ser Phe Trp Ala Ser Phe Ala
            100                 105                 110

Leu Gln Phe Val Asn Val Lys Ile Ile Leu Tyr Gly Val Thr Ala Leu
        115                 120                 125

Ser Thr Phe Val Leu Pro Gln Thr Gln Ala Leu Ser Trp Val Val Gly
    130                 135                 140

Val Ser Val Leu Leu Ala Met Ile Gly Thr Phe Gly Asn Val Cys Trp
145                 150                 155                 160

Ala Leu Ala Gly His Leu Phe Gln Arg Leu Phe Arg Gln Tyr Gly Arg
                165                 170                 175

Gln Leu Asn Ile Val Leu Ala Leu Leu Leu Val Tyr Cys Ala Val Arg
            180                 185                 190

Ile Phe Tyr
        195

<210> SEQ ID NO 15
<211> LENGTH: 636
<212> TYPE: DNA
<213> ORGANISM: Escherichia coli
<220> FEATURE:
<221> NAME/KEY: CDS
<222> LOCATION: (1)..(636)

<400> SEQUENCE: 15 gtg ttt tct tat tac ttt caa ggt ctt gca ctt ggg gcg gct atg atc    48
Val Phe Ser Tyr Tyr Phe Gln Gly Leu Ala Leu Gly Ala Ala Met Ile
1               5                   10                  15
```

```
cta ccg ctc ggt cca caa aat gct ttt gtg atg aat cag ggc ata cgt      96
Leu Pro Leu Gly Pro Gln Asn Ala Phe Val Met Asn Gln Gly Ile Arg
         20                  25                  30 cgt cag tac cac att atg att gcc tta ctt tgt gct atc agc gat ttg     144
Arg Gln Tyr His Ile Met Ile Ala Leu Leu Cys Ala Ile Ser Asp Leu
             35                  40                  45 gtc ctg att tgc gcc ggg att ttt ggt ggc agc gcg tta ttg atg cag     192
Val Leu Ile Cys Ala Gly Ile Phe Gly Gly Ser Ala Leu Leu Met Gln
 50                  55                  60 tcg ccg tgg ttg ctg gcg ctg gtc acc tgg ggc ggc gta gcc ttc ttg     240
Ser Pro Trp Leu Leu Ala Leu Val Thr Trp Gly Gly Val Ala Phe Leu
 65                  70                  75                  80 ctg tgg tat ggt ttt ggc gct ttt aaa aca gca atg agc agt aat att     288
Leu Trp Tyr Gly Phe Gly Ala Phe Lys Thr Ala Met Ser Ser Asn Ile
                 85                  90                  95 gag tta gcc agc gcc gaa gtc atg aag caa ggc aga tgg aaa att atc     336
Glu Leu Ala Ser Ala Glu Val Met Lys Gln Gly Arg Trp Lys Ile Ile
                100                 105                 110 gcc acc atg ttg gca gtg acc tgg ctg aat ccg cat gtt tac ctg gat     384
Ala Thr Met Leu Ala Val Thr Trp Leu Asn Pro His Val Tyr Leu Asp
                115                 120                 125 act ttt gtt gta ctg ggc agc ctt ggc ggg caa ctt gat gtg gaa cca     432
Thr Phe Val Val Leu Gly Ser Leu Gly Gly Gln Leu Asp Val Glu Pro
        130                 135                 140 aaa cgc tgg ttt gca ctc ggg aca att agc gcc tct ttc ctg tgg ttc     480
Lys Arg Trp Phe Ala Leu Gly Thr Ile Ser Ala Ser Phe Leu Trp Phe
145                 150                 155                 160 ttt ggt ctg gct ctt ctc gca gcc tgg ctg gca ccg cgt ctg cgc acg     528
Phe Gly Leu Ala Leu Leu Ala Ala Trp Leu Ala Pro Arg Leu Arg Thr
                165                 170                 175 gca aaa gca cag cgc att atc aat ctg gtt gtg gga tgt gtt atg tgg     576
Ala Lys Ala Gln Arg Ile Ile Asn Leu Val Val Gly Cys Val Met Trp
            180                 185                 190 ttt att gcc ttg cag ctg gcg aga gac ggt att gct cat gca caa gcc     624
Phe Ile Ala Leu Gln Leu Ala Arg Asp Gly Ile Ala His Ala Gln Ala
        195                 200                 205 ttg ttc agt tag                                                     636
Leu Phe Ser
    210

<210> SEQ ID NO 16
<211> LENGTH: 211
<212> TYPE: PRT
<213> ORGANISM: Escherichia coli

<400> SEQUENCE: 16

Val Phe Ser Tyr Tyr Phe Gln Gly Leu Ala Leu Gly Ala Ala Met Ile
 1               5                  10                  15

Leu Pro Leu Gly Pro Gln Asn Ala Phe Val Met Asn Gln Gly Ile Arg
             20                  25                  30

Arg Gln Tyr His Ile Met Ile Ala Leu Leu Cys Ala Ile Ser Asp Leu
         35                  40                  45

Val Leu Ile Cys Ala Gly Ile Phe Gly Gly Ser Ala Leu Leu Met Gln
 50                  55                  60

Ser Pro Trp Leu Leu Ala Leu Val Thr Trp Gly Gly Val Ala Phe Leu
 65                  70                  75                  80

Leu Trp Tyr Gly Phe Gly Ala Phe Lys Thr Ala Met Ser Ser Asn Ile
                 85                  90                  95
```

```
Glu Leu Ala Ser Ala Glu Val Met Lys Gln Gly Arg Trp Lys Ile Ile
            100                 105                 110

Ala Thr Met Leu Ala Val Thr Trp Leu Asn Pro His Val Tyr Leu Asp
        115                 120                 125

Thr Phe Val Val Leu Gly Ser Leu Gly Gly Gln Leu Asp Val Glu Pro
    130                 135                 140

Lys Arg Trp Phe Ala Leu Gly Thr Ile Ser Ala Ser Phe Leu Trp Phe
145                 150                 155                 160

Phe Gly Leu Ala Leu Leu Ala Ala Trp Leu Ala Pro Arg Leu Arg Thr
                165                 170                 175

Ala Lys Ala Gln Arg Ile Ile Asn Leu Val Val Gly Cys Val Met Trp
            180                 185                 190

Phe Ile Ala Leu Gln Leu Ala Arg Asp Gly Ile Ala His Ala Gln Ala
        195                 200                 205

Leu Phe Ser
    210

<210> SEQ ID NO 17
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 17
gtgtggaacc gacgccggat                                            20

<210> SEQ ID NO 18
<211> LENGTH: 23
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 18
tgttgtatgg tacggggttc gag                                        23

<210> SEQ ID NO 19
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 19
ctttgccaat cccgtctccc                                            20

<210> SEQ ID NO 20
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
      DNA

<400> SEQUENCE: 20
gccccatgca taacggaaag                                            20
```

<210> SEQ ID NO 21
<211> LENGTH: 26
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
     DNA

<400> SEQUENCE: 21
gaagatcttg taggccggat aaggcg                                        26

<210> SEQ ID NO 22
<211> LENGTH: 20
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
     DNA

<400> SEQUENCE: 22
tggttttacc aattggccgc                                               20

<210> SEQ ID NO 23
<211> LENGTH: 21
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
     DNA

<400> SEQUENCE: 23
acttctcccg cgagccagtt c                                             21

<210> SEQ ID NO 24
<211> LENGTH: 21
<212> TYPE: DNA
<213> ORGANISM: Artificial Sequence
<220> FEATURE:
<221> NAME/KEY: misc_feature
<223> OTHER INFORMATION: Description of Artificial Sequence: synthetic
     DNA

<400> SEQUENCE: 24
ggcaagctta gcgcctctgt t                                             21
```